United States Patent [19]

Robertson

[11] 4,088,658

[45] May 9, 1978

[54] SYNTHESIS OF DIDEOXYZEARALANE AND RELATED COMPOUNDS

[75] Inventor: Donald Edwin Robertson, Terre Haute, Ind.

[73] Assignee: IMC Chemical Group, Inc., Terre Haute, Ind.

[21] Appl. No.: 738,929

[22] Filed: Nov. 4, 1976

[51] Int. Cl.² .......................................... C07D 313/00
[52] U.S. Cl. ................................................. 260/343.41
[58] Field of Search ..................... 260/343.2 F, 343.41

[56] References Cited

U.S. PATENT DOCUMENTS 3,887,583   6/1975   Wehrmeister et al. ........ 260/343.2 F

OTHER PUBLICATIONS

Wagner & Zook, Synthetic Org. Chem., p. 823.
March Advanced Org. Chem., p. 505.
Kenner et al. Chemical Abstracts 44, p. 565c, 1950.
Kenner et al. J. Chem. Soc., p. 406, 1950.

*Primary Examiner*—Natalie Trousof
*Assistant Examiner*—Jane T. Fan
*Attorney, Agent, or Firm*—E. A. Figg; H. E. Post

[57] ABSTRACT

A method is disclosed for preparing dideoxyzearalane and related compounds which comprises reacting an appropriate hydroxy compound with an organic sulfonyl chloride to form a sulfonate ester derivative; recovering the sulfonate ester derivative; and catalytically hydrogenolyzing the sulfonate ester derivative to form the desired product.

6 Claims, No Drawings

SYNTHESIS OF DIDEOXYZEARALANE AND RELATED COMPOUNDS

This invention relates to the synthesis of dideoxyzearalane and related compounds (hereinafter sometimes referred to as deoxyzearalane type compounds). More particularly, the invention relates to a method for preparing a deoxyzearalane type compound of the formula

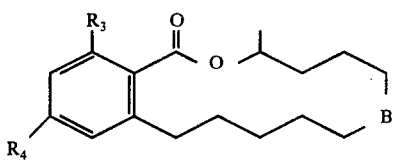

which comprises reacting a hydroxy compound of the formula

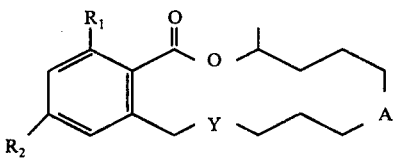

with an organic sulfonyl chloride of the formula $RSO_2Cl$ under esterifying conditions to form a sulfonate ester derivative; recovering the sulfonate ester derivative; and catalytically hydrogenolyzing the sulfonate ester derivative to form the deoxyzearalane type compound; wherein A is selected from the group consisting of —$CH_2$—, >C=O, >CHOH, and >$CHOR_5$; B is the same as A except when A is >CHOH, B is —$CH_2$—; Y may be a single bond or a double bond; $R_1$ and $R_2$ are each selected from the group consisting of —H, —OH, and —$OR_5$, provided that at least one of $R_1$ and $R_2$ is —OH, $R_3$ and $R_4$ are the same as $R_1$ and $R_2$ respectively, except when $R_1$ or $R_2$ is —OH, the corresponding $R_3$ or $R_4$ is —H; $R_5$ may be lower alkyl of from 1 to about 6 carbon atoms, such as methyl, ethyl, propyl, butyl, pentyl, hexyl, etc.; lower alicyclic of from about 4 to about 8 carbon atoms, such as cyclobutyl, cyclohexyl, cyclooctyl, etc.; lower acyl of from 1 to about 6 carbon atoms, such as formyl, acetyl, butyryl, etc.; monocyclic aryl of about 6 to 8 carbon atoms, such as phenyl, tolyl, etc.; and monocyclic aralkyl, that is, an alkyl group with an aryl substituent thereon, wherein the alkyl group has 1 to about 5 carbon atoms and the aryl group has about 6 to 8 carbon atoms, such as benzyl, tolylmethyl, etc.; and R is selected from the group consisting of lower alkyl of from 1 to about 10 carbon atoms, such as methyl, ethyl, butyl, octyl, 2-ethylhexyl, decyl, etc., and aryl such as phenyl, p-tolyl, and p-bromophenyl.

Heretofore, the primary method of preparing deoxyzearalane type compounds has been by selectively etherifying an appropriate hydroxy compound with a heterocyclic compound, such as 2-chlorotetrazole, 2-chlorobenzoxazole, or 1-phenyl-5-chlorotetrazole; then cleaving the heterocyclic ether radicals by catalytic hydrogenolysis to provide the desired deoxyzearalane type compound. The above method and the utility of deoxyzearalane type compounds as anabolic and estrogenic agents in animals are disclosed in U.S. Pat. No. 3,887,583, Wehrmeister, H. L., et al., June 3, 1975.

The method of the present invention is advantageous over prior art methods, because inter alia, the reactant, the organic sulfonyl chloride, is generally more readily available and is currently less costly than the heterocyclic compounds of the prior art method.

The hydroxy compounds used as starting materials for the method of the present invention include zearalenone, represented by the following structural formula:

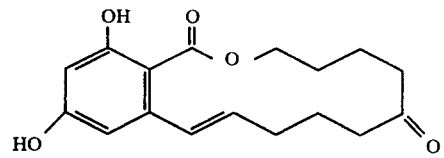

and compounds derived from zearalenone by known methods. Zearalenone is a natural metabolite of the organism, *Gibberella zeae*, and may be prepared by cultivation of a zearalenone-producing strain of that microorganism on a suitable nutrient medium, as taught, for instance, by Andrews, F. N., et al., U.S. Pat. No. 3,196,019, July 20, 1965. The nomenclature used herein generally conforms to that described by Shipchandler, M. T., *Heterocycles* 3, 471 (1975).

In a preferred embodiment, the present method produces deoxyzearalane type compounds of the formula:

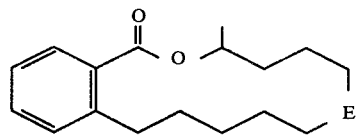

comprising the steps of reacting a hydroxy compound of the formula

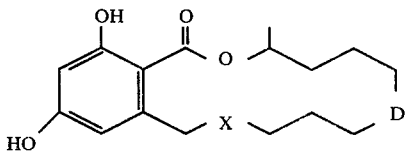

with an organic sulfonyl chloride of the formula $R\ SO_2\ Cl$ under esterifying conditions to form a sulfonate ester derivative of the formula

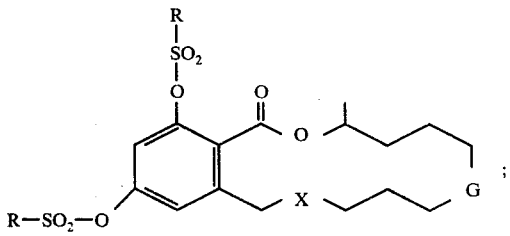

recovering the sulfonate ester derivative; and catalytically hydrogenolyzing the sulfonate ester derivative to form the deoxyzearalane type compound, wherein D is selected from the group consisting of —$CH_2$—, >C=O, and >CHOH; E is the same as D except when D is >CHOH, E is —CH$_2$—; X may be a single bond or a double bond; G is the same as D, except when D is >CHOH, G is >CH—O—SO$_2$R; and R is selected from the group consisting of lower alkyl of from 1 to about 5 carbon atoms, phenyl, p-tolyl, and p-bromophenyl.

Examples of the method of the present invention are represented by the following reactions.

A. Conversion of zearalane to dideoxyzearalane.

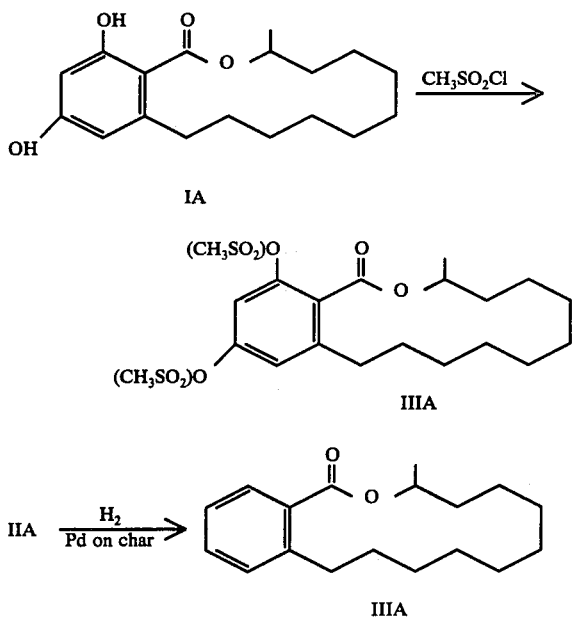

B. Conversion of zearalanol to dideoxyzearalane.

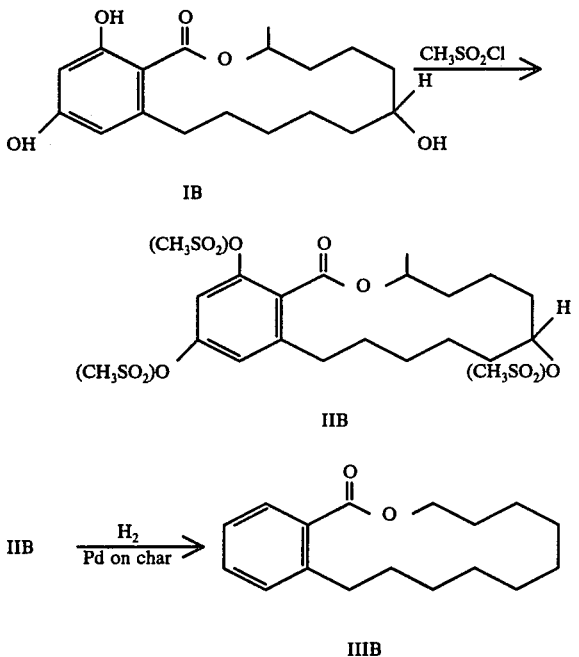

C. Conversion of zearalenone to dideoxyzearalanone.

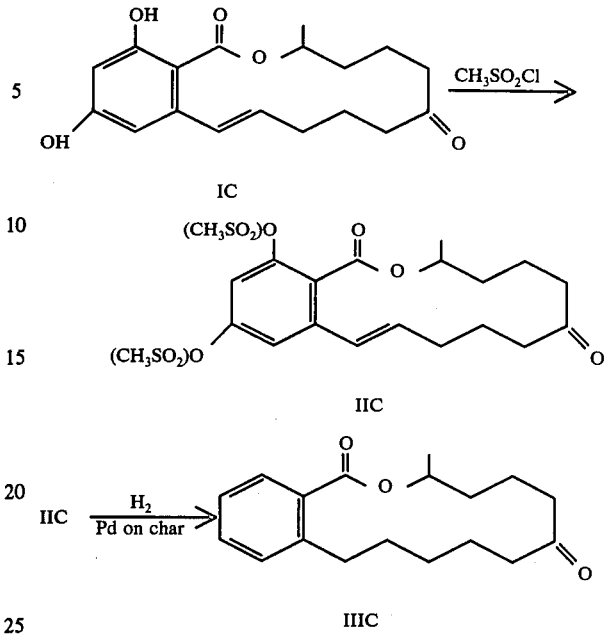

The organic sulfonyl chloride may be an alkane sulfonyl chloride containing from 1 to about 10 carbon atoms, or an aryl sulfonyl chloride such as benzene sulfonyl chloride, toluene sulfonyl chloride, or p-bromobenzene sulfonyl chloride. Preferred organic sulfonyl chlorides are alkane sulfonyl chlorides containing from 1 to about 5 carbon atoms, the most preferred being methane sulfonyl chloride.

The reaction of the organic sulfonyl chloride with the hydroxy compound to form a sulfonate ester derivative is conducted under esterifying conditions. Such esterifying conditions advantageously include conducting the reaction in a non-reactive solvent, i.e., a solvent which does not react with the reactants or products or otherwise deleteriously affect the reaction. Such solvents generally include aromatic or lower aliphatic organic solvents which do not contain active hydrogens, e.g., normally liquid aliphatic hydrocarbons, of from about 6 to about 10 carbon atoms, such as cyclohexane, octane, decane, etc.; aliphatic ethers of from about 4 to about 10 carbon atoms, such as tetrahydrofuran, dipropyl ether, dibutyl ether, etc.; aromatic hydrocarbons of from about 6 to 10 carbon atoms, such as benzene, toluene, xylene, pyridine, etc.; tertiary aliphatic amines of from 6 to about 10 carbon atoms, such as triethylamine, tripropylamine, etc.; and aliphatic ketones of from about 3 to about 8 carbon atoms, such as acetone, methyl ethyl ketone, dibutyl ketone, etc.

The reaction medium also advantageously includes a base in an amount sufficient to neutralize liberated hydrogen chloride and catalyze the reaction, i.e., an amount at least equivalent to the organic sulfonyl chloride. The base is advantageously an organic base such as pyridine or a tertiary lower aliphatic amine, e.g. amines having from about 6 to 10 carbon atoms such as triethyl amine, tripropyl amine, etc. The preferred base is pyridine, which can be effectively used as both the solvent and the base.

The reaction temperature is not critical; however, the time required for substantially complete reaction may vary, with the temperature. Generally, the reaction temperature is from about 0° to about 75° C, preferably from about 20° to about 50° C. The reaction is usually complete within about 24 hours at about room temperature or less at elevated temperatures.

The resulting sulfonate ester derivative is recovered from the reaction mixture by any suitable method, such as crystallization or extraction. The preferred method of recovering the sulfonate ester derivative is to mix the reaction mixture with cold water, then extract the water mixture with a suitable immiscible solvent such as methylene chloride or chloroform. The extract is then dried, e.g., with $Na_2SO_4$, and the solvent removed by evaporation or distillation at reduced pressure. The resulting product may be further purified by recrystallization.

The sulfonate ester derivative is catalytically hydrogenolyzed to provide the desired deoxyzearalane type compound. The hydrogenolysis reaction is generally conducted at an elevated temperature and pressure, therefore, a sealed pressure reaction vessel, such as a "bomb" type reactor or an autoclave, is advantageously employed.

The hydrogenolysis reaction temperature is generally from about 100° to about 250° C, preferably from about 150° to about 230° C. The hydrogenolysis is advantageously conducted in a non-reactive solvent containing a proton acceptor. Suitable solvents include lower aliphatic alcohols, ketones, and ethers, e.g., methanol, ethanol, propanol, acetone, methyl ethyl ketone, dioxane, tetrahydrofuran, etc.; aromatic solvents, e.g., benzene, toluene, pyridine, any isomeric form of lutidine, e.g., 2,3-lutidine, 2,4-lutidine, 2,5-lutidine, 2,6-lutidine, 3,4-lutidine or 3,5-lutidine, etc.; and tertiary lower aliphatic amines, e.g., triethylamine, tripropylamine, etc. The proton acceptor is preferably an organic nitrogen compound such as pyridine, lutidine, or tertiary lower aliphatic amines of from about 6 to 10 carbon atoms, e.g., triethylamine, tripropylamine, etc. The proton acceptor is advantageously employed in a molar amount at least equivalent to the organic sulfonate ester groups. The proton acceptor may be employed as the solvent for the reaction. The most preferred proton acceptor is triethylamine.

The hydrogenolysis reaction may be catalyzed by catalytic amounts of any suitable catalyst. Preferred catalysts are platinum, palladium, and Raney nickel. Platinum and palladium catalysts may be finely divided or may be deposited on finely divided carbon. The most preferred catalyst is palladium deposited on finely divided carbon, containing from about 1 to about 10% by wt. palladium. An approximately 5% palladium on carbon catalyst is preferably employed at a concentration of from about 0.05 to 5 g per gram of sulfonate ester derivative, preferably about 0.2 g to 2.5 g per grams of sulfonate ester derivative.

The hydrogenolysis reaction is conducted under a hydrogen atmosphere at an elevated pressure. The hydrogen pressure is advantageously from about 200 to about 1000 pounds per square inch (about 14.1 to about 70.4 kg per square centimeter), preferably from about 400 to about 600 pounds per square inch (about 28.2 to about 42.2 kg per square centimeter).

The resulting deoxyzearalane type compound may be recovered from the reaction mixture by any suitable method. A convenient method of recovery is to remove the catalyst, e.g., by filtration, decantation, or centrifugation; concentrate the liquid portion, e.g., by evaporation or vacuum distillation; extract the residue with a mixture of water and a water immiscible solvent, such as methylene chloride or chloroform; separate the solvent layer; and remove the solvent, e.g., by evaporation or vacuum distillation. The residue may be further purified, e.g., by recrystallization, if desired.

The invention is further illustrated by the following examples which are not intended to be limiting.

EXAMPLE I

To a solution of zearalane (3.06 g, 0.010 mole) in anhydrous pyridine (10 ml) at 28° was added rapidly methanesulfonyl chloride (2.52 g, 1.8 ml, 0.022 mole). The solution was heated at 50°–60° for 6.0 hours. Methanesulfonyl chloride (0.5 ml) was added and the heating continued for 3.5 hours. TLC analysis showed very little zearalane remaining after 9 hours. The cooled solution was poured into ice-cold water. An oil formed. The mixture was made acidic with HCl and extracted with $CH_2Cl_2$ (4 × 100 ml portions). The extracts were washed with water (2 × 100 ml portions), dried ($Na_2SO_4$) and concentrated in vacuum yielding 4.82 g (104% of theory) of a brown oil. NMR analysis of the crude product showed it to be diester with residual solvent present. The crude product was recrystallized from isopropanol (100 ml) yielding 3.41 g (73.8% of theory) of a yellow powder: mp 102°–103°. The TLC was homogeneous and less polar than starting material. The NMR spectrum was consistent with the structure of $O^2,O^4$-dimethanesulfonylzearalane. The following elemental analysis was obtained. Calculated for $C_{20}H_{32}O_8S_2$: C, 51.93; H, 6.54; O, 27.67; S, 13.86. Found: C, 51.74; H, 6.19; O, 27.38; S, 13.88.

A solution of $O^2,O^4$-dimethanesulfonylzearalane (0.92 g, 0.002 mole, mp 99°–100°) in anhydrous methanol (300–400 ml) containing triethylamine (0.56 ml, 0.41 g, 0.004 mole) was hydrogenated in a Parr Pressure Reactor (2000 ml capacity) over palladium (0.5 g, 5% Pd/C) at 150°, initial pressure of 500 psi (35.2 kg/cm$^2$) at 25° (maximum pressure 840 psi (59.1 Kg/cm$^2$) at 150°) during 17.5 hours. The catalyst was removed by filtration and washed with methanol (100 ml). The filtrate and washes were concentrated under reduced pressure yielding a residue that was shaken with a mixture of $CH_2Cl_2$ (50 ml) and $H_2O$ (50 ml). The $CH_2Cl_2$ layer was separated and washed with water (50 ml), 0.2 N HCl (50 ml), water (50 ml), 5% cold aqueous NaOH (2 × 50 ml portions) and water (50 ml). The $CH_2Cl_2$ solution was dried ($Na_2SO_4$) and concentrated in vacuum yielding 0.51 g (93% of theory) of yellow oil. TLC showed two components with least polar corresponding to dideoxyzearalane. The oil was analyzed by high pressure liquid chromatography which indicated a 28.8% conversion to dideoxyzearalane. The NMR spectrum confirmed the presence of dideoxyzearalane.

EXAMPLE II

To a solution of the high-melting isomer of zearalanol (32.24 g, 0.10 mole), in pyridine (500 ml) at room temperature was added methanesulfonyl chloride(45.8 g, 31 ml, 0.40 mole) during 3–4 minutes. The temperature rose to 40°. The solution was stirred at ambient temperatures for 22 hours and poured into ice-cold 3.8 M HCl (2000 ml). The gummy precipitate was collected by filtration. The cake and other solids adhering to the flask were taken up in $CH_2Cl_2$ (700 ml). The solution was washed with water (2 × 300 ml portions), dried ($Na_2SO_4$) and diluted with methanol (1500 ml). The solution was concentrated at 40°–50° in vacuum until precipitation occurred. The solution was warmed until clear and allowed to cool yielding 38.14 g, (68.5% of theory) of pale yellow crystals: mp 128°-130°. Concentration of the filtrate to ca. 75 ml yielded an additional 12.7 g (22.8% of theory) of pale yellow crystals: mp 80°-82° C.

Other runs of the above procedure produced product mp 114°-115°. Recrystallization of a 5 g sample of this material yielded 4.37 g of white crystals: mp 131°-132° C to a clear melt that turned red at 140°-145° C, the NMR spectrum was consistent with the structure of $O^2,O^4,O^{6'}$-trimethanesulfonylzearalane.

A solution of $O^2,O^4,O^{6'}$-trimethanesulfonylzearalane (1.01 g, 0.002 mole, mp 130°-131.5°) in triethylamine (400 ml) was hydrogenated in a Parr Pressure Reactor (2000 ml capacity) over palladium (0.5 g, 5% Pd/C) at 150° under an initial pressure of 500 psi (35.2 kg/cm²) at 25° (max pressure was 720 psi (50.7 kg/cm²) at 150°) during 9 hours. The catalyst was removed by filtration and washed with methanol (200 ml), $CH_2Cl_2$ (200 ml) and acetone (200 ml). The filtrate and washes were concentrated in vacuum and the residue was shaken with a mixture of $CH_2Cl_2$ (100 ml) and water (100 ml). The $CH_2Cl_2$ layer was separated and the aqueous layer was extracted with $CH_2Cl_2$ (100 ml). The combined $CH_2Cl_2$ extracts were washed with brine (2×100 ml portions), 2 N HCl (2×50 ml portions) and water (2×100 ml portions). The $CH_2Cl_2$ solution was dried ($Na_2SO_4$) and concentrated in vacuum yielding 0.49 g (89% of theory) of a brown oil: TLC showed 2 components with least polar corresponding to dideoxyzearalane. High pressure liquid chromatography indicated 77.3 wt. % dideoxyzearalane content corresponding to a 69% conversion. The NMR spectrum was identical with that of dideoxyzearalane except for some impurities.

EXAMPLE III

To a solution of zearalenone (31.8 g, 0.10 mole) in pyridine (300 ml) at room temperature was added rapidly during 1-2 minutes methanesulfonyl chloride (34.5 g, 23 ml, 0.30 mole). The solution was stirred for 6 hours at 50°-60°. Additional methanesulfonyl chloride (5 ml) was added and heating was continued for 16 hours. The solution was cooled and poured into 5.2 M HCl (900 ml). The mixture was extracted with $CH_2Cl_2$ (4×500 ml portions). The extracts were washed with water (3×500 ml portions), dried ($Na_2SO_4$) and concentrated in vacuum yielding 43.52 g (91% of theory) of tan solid. Recrystallization of a 5 g sample from $CH_2Cl_2$ (50 ml) and methanol (100 ml) with some concentration at 40° C yielded in two crops 4.33 g (79% of theory) of white crystals: mp 179°-180°. The TLC was homogeneous. The IR and NMR spectra were consistent with the structure of $O^2,O^4$-dimethanesulfonylzearalenone. The product was further dried in vacuum at 80° for elemental analysis. The following elemental analysis was obtained. Calculated for $C_{20}H_{26}O_9S_2$: C, 50.61%; H, 5.52%; S, 13.52%. Found: C, 50.71%; H, 5.42%; S, 13.43%.

To a solution of $O^2,O^4$-dimethanesulfonylzearalenone (0.002 mole, 0.95 gram), in methanol containing triethylamine was added palladium catalyst on char and the mixture placed in a hydrogenation bomb where hydrogen was admitted to an initial pressure of 500 psi (35.2 kg/cm²) and the bomb heated to 150° C. The compound dideoxyzearalanone was recovered in 12% yield.

EXAMPLE IV

The experiment of Example I is repeated in all essential details except zearalanone is substituted for zearalane and ethanesulfonyl chloride is substituted for methane sulfonyl chloride. The experiment should yield dideoxyzearalanone.

EXAMPLE V

The experiment of Example I is repeated in all essential details except $O^2$-benzylzearalane is substituted for zearalane and butanesulfonyl chloride is substituted for methanesulfonyl chloride. A compound of the following formula should be recovered:

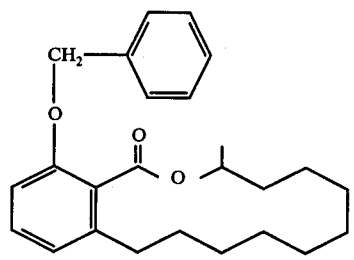

EXAMPLE VI

The experiment of Example I is repeated in all essential details except $O^4,O^{6'}$-diethylzearalanol is substituted for zearalane and propanesulfonyl chloride is substituted for methanesulfonyl chloride. A compound of the following formula should be recovered:

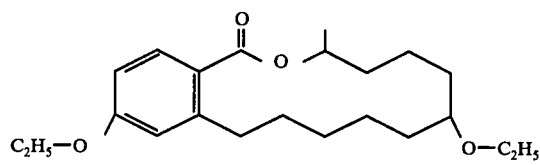

EXAMPLE VII

The experiment of Example I is repeated in all essential details, except p-toluenesulfonyl chloride is substituted for methane sulfonyl chloride. Dideoxyzearalane should be recovered.

EXAMPLE VIII

The experiment of Example I is repeated in all essential details, except p-bromobenzene sulfonyl chloride is substituted for methane sulfonyl chloride. Dideoxyzearalane should be recovered.

EXAMPLE IX

This example exhibits data obtained on the utility of (S)-dideoxyzearalane as an oral growth promoting agent for steers and heifers.

Table I

| | Effect of Orally Administered (S)-Dideoxyzearalane on Gain in Weight of Cattle | | |
|---|---|---|---|
| Item | Test A | Test B | Test C |
| Sex of Animals | Steers | Steers | Heifers |
| Number of Animals | 40 | 207 | 80 |

Table I-continued
Effect of Orally Administered (S)-Dideoxyzearalane on Gain in Weight of Cattle

| Item | Test A | Test B | Test C |
|---|---|---|---|
| Age at Start of Experiment | 9 Months | 12 Months | 12–15 Months |
| Breed | #1 Crossbred British Brahman | #1 Okie | Majority Hereford |
| Initial Weight | 215 Kg. | 700 Lb. | 194 Kg. |
| Duration of Test | 73 Days | 70 Days | 112 Days |
| Location | Thermal, CA | Panhandle, TX | Monterrey, Mexico |
| Results | | | |
| 10 mg/head/day | | 1.0% Gain | |
| 20 mg/head/day | | 7.2% Gain | 12.9% Gain |
| 40 mg/head/day | 2.3% Gain | 11.4% Gain | 11.5% Gain |
| 60 mg/head/day | 3.4% Gain | | 7.3% Gain |
| 80 mg/head/day | 7.6% Gain | | |

NOTE:
The results are reported in terms of percentage gain of the test group compared to the control group. Statistical treatment of the raw data gave the following results:
Test A - None of the responses were significant at P <0.05.
Test B - Growth response at the highest level was significant at P <0.01.
Test C - The gain at the 20 mg level was significant at P <0.05. The combined effect of all treatments gave highly significant response at P <0.01.

I claim:
1. A method for preparing a deoxyzearalane type compound of the formula

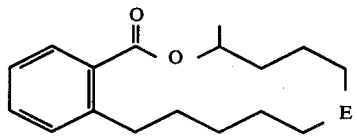

comprising reacting a hydroxy compound of the formula

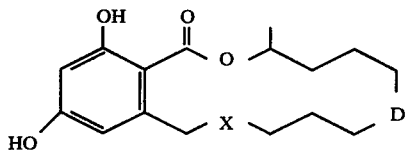

with an organic sulfonyl chloride of the formula

RSO$_2$Cl under esterifying conditions which conditions include a non-reactive, aromatic or lower aliphatic organic reaction solvent containing an organic base selected from the group consisting of pyridine and tertiary lower aliphatic amines of from about 6 to 10 carbon atoms in an amount at least equimolar to the organic sulfonyl chloride; and a reaction temperature of from about 0° to about 75° C, to form a sulfonate ester derivative of the formula

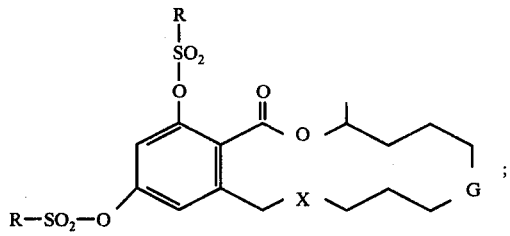

recovering the sulfonate ester derivative; and catalytically hydrogenolyzing the sulfonate ester derivative at a temperature of from about 100° to about 250° C at a hydrogen pressure of from about 200 to about 1000 pounds per square inch (about 14.1 to about 70.4 kilograms per square centimeter), in the presence of a catalyst selected from the group consisting of platinum, palladium, and Raney nickel, in a non-reactive, aromatic or lower aliphatic organic solvent containing a proton acceptor selected from the group consisting of pyridine, any isomeric form of lutidine, and tertiary lower aliphatic amines of from about 6 to 10 carbon atoms in an amount at least equivalent to the alkyl sulfonate ester groups, thereby forming the deoxyzearalane type compound; wherein D is selected from the group consisting of —CH$_2$—, >C=O, and >CHOH; E is the same as D except when D is >CHOH, E is —CH$_2$—; X may be a single bond or a double bond; G is the same as D, except when D is >CHOH, G is >CH—O—SO$_2$R; and R is selected from the group consisting of lower alkyl of from 1 to about 5 carbon atoms.

2. The method of claim 1 wherein the esterifying conditions include a non-reactive organic reaction solvent selected from the group consisting of cyclopentane, octane, tetrahydrofuran, benzene, pyridine, and triethylamine, said reaction solvent containing an organic base selected from the group consisting of pyridine and triethylamine in an amount at least equimolar to the alkyl sulfonyl chloride, and a reaction temperature of from about 20° to about 50° C; and the catalytic hydrogenolysis is conducted at a temperature of from about 150° to about 230° C at a hydrogen pressure of from about 400 to about 600 pounds per square inch (about 28.2 to about 42.2 kilograms per square centimeter), in the presence of a catalyst of palladium deposited on finely divided carbon containing from about 1% to about 10% by wt. palladium, said catalyst being employed at a concentration of from about 0.2 g to about 2.5 g per gram of sulfonate ester derivative, said hydrogenolysis being conducted in a non-reactive organic solvent selected from the group consisting of methanol, ethanol, propanol, acetone, methyl ethyl ketone, dioxane, tetrahydrofuran, benzene, toluene, pyridine, lutidine and triethylamine, said organic solvent containing a proton acceptor selected from the group consisting of pyridine, lutidine, and triethyl amine in a molar amount at least equivalent to the organic sulfonate ester groups.

3. The method of claim 2 wherein the deoxyzearalane type compound prepared by the method is dideoxyzearalane, the hydroxy compound is zearalane and the organic sulfonyl chloride is methanesulfonyl chloride.

4. The method of claim 2 wherein the deoxyzearalane type compound prepared by the method is dideoxyzearalanone, the hydroxy compound is zearalenone, and the organic sulfonyl chloride is ethanesulfonyl chloride.

5. The method of claim 2 wherein the deoxyzearalane type compound prepared by the method is dideoxyzearalane, the hydroxy compound is zearalanol, and the organic sulfonyl chloride is butane sulfonyl chloride.

6. The method of claim 2 wherein the deoxyzearalane type compound prepared by the method is dideoxyzearalanone, the hydroxy compound is zearalanone, and the organic sulfonyl chloride is pentane sulfonyl chloride.

* * * * *

UNITED STATES PATENT AND TRADEMARK OFFICE
CERTIFICATE OF CORRECTION

PATENT NO. : 4,088,658
DATED : May 9, 1978
INVENTOR(S) : Donald E. Robertson

It is certified that error appears in the above-identified patent and that said Letters Patent are hereby corrected as shown below:

Column 1, line 25, that portion of the formula reading $\diagup Y \diagdown$ should read $\diagdown Y \diagup$ Column 2, line 45, that portion of the formula reading $\diagup X \diagdown$ should read $\diagdown X \diagup$ Column 2, line 61, that portion of the formula reading $\diagup X \diagdown$ should read $\diagdown X \diagup$ Column 9, line 37, that portion of the formula reading $\diagup X \diagdown$ should read $\diagdown X \diagup$ Column 9, line 60, that portion of the formula reading $\diagup X \diagdown$ should read $\diagdown X \diagup$ Signed and Sealed this Twenty-sixth Day of December 1978

[SEAL]

Attest:

RUTH C. MASON
Attesting Officer

DONALD W. BANNER
Commissioner of Patents and Trademarks